United States Patent [19]
Kretzschmar et al.

[11] Patent Number: 5,780,640
[45] Date of Patent: Jul. 14, 1998

[54] PROCESS FOR THE BIOTECHNOLOGICAL PREPARATION OF L-THIENYLALANINES IN ENANTIOMERICALLY PURE FORM FROM 2-HYDROXY-3-THIENYLACRYLIC ACIDS AND THEIR USE

[75] Inventors: Gerhard Kretzschmar, Eschborn; Johannes Meiwes, Idstein; Manfred Schudok, Hattersheim/Main; Peter Hammann, Babenhausen; Ulrich Lerch, Hofheim/Taunus; Susanne Grabley, Königstein/Taunus, all of Germany

[73] Assignee: Hoechst Aktiengesellschaft, Frankfurt am Main, Germany

[21] Appl. No.: 465,311

[22] Filed: Jun. 5, 1995

Related U.S. Application Data

[62] Division of Ser. No. 99,352, Jul. 29, 1993, Pat. No. 5,480,786.

[30] Foreign Application Priority Data

Jul. 31, 1992 [DE] Germany ................ 42 25 280.6

[51] Int. Cl.$^6$ ............... C07D 239/10; C07D 233/64; C07D 333/04
[52] U.S. Cl. ............... 548/315.1; 549/29; 549/81
[58] Field of Search ............... 548/315.1; 549/29

[56] References Cited

U.S. PATENT DOCUMENTS 3,971,700  7/1976  Roesten .

FOREIGN PATENT DOCUMENTS

| | | |
|---|---|---|
| 1323629 | 10/1993 | Canada . |
| 0 152 275 A2 | 8/1985 | European Pat. Off. . |
| 0 152 275 B1 | 8/1985 | European Pat. Off. . |
| 0 189 938 A2 | 8/1986 | European Pat. Off. . |
| 0 248 357 A2 | 12/1987 | European Pat. Off. . |
| 0 248 357 A3 | 12/1987 | European Pat. Off. . |
| 2800596 | 7/1978 | Germany . |
| 676846 A5 | 3/1991 | Switzerland . |
| WO 89/12688 | 12/1989 | WIPO . |

OTHER PUBLICATIONS

Enzyme Nomenclature, pp. 220, 222 (1984).
Hruban et al. "Effects of Some Phenylalanine Analogs upon Protein Metabolism in Vivo", Laboratory Investigation 14(5) 1965.
EPO Search Report for EP 93 11 2006, Dec. 4, 1994.
Bladon, C.M., "Synthesis of Heteroaromatic Thyrotropin--releasing Hormone Analogues," J. Chem. Soc. Perkin Trans 1:1151–58 (1990).
Cooper, A.J.L., et al., "Synthesis and Properties of the α–Keto Acids," Chem. Rev. 83:321–58 (1983).
Horner, L., et al., "α–Methoxy–, α–Äthylmercapto–und α–Dimethylamino–acrylester aus Substituierten Essigestern mit Aldehyden," Liebigs Ann. Chem. 703:37–43 (1967).
Sheldon, R.A., et al., "the Synthesis of Angiotensin–Converting Enzyme (ACE) Inhibitors." Chimicaoggi 35–47 (May 1991).
Chibata, I., et al., "Use of Immobilized Cells." Ann. Rev. Biophys. Bioeng. 10:197–216 (1981).
Syldatk, C., et al., "Production of Optically Pure D–and L–α–Amino Acids by Bioconversion of D,L–5–Monosubstituted Hydantoin Derivatives," Advances in Biochem. Eng./Biotech. 41:29–75 (1990).
Möller, A., et al., "Stereo–and Substrate–Specificity of a D–Hydantoinase and a D–N–carbamyl–amino Acid Amidohydrolase of *Arthrobacter crystallopoietes* AM 2," Enzyme Microb. Tech. 10:618–25 (1988).
Wichmann, R., et al., "Continuous Microbial Production of L–leucine with Cell Retention," Appl. Microbiol. Biotech. 32:373–79 (1990).
Ng, S.C., et al., "Simple Purification Procedure for L–α–Amino Acids Generated by Enzymatic Transamination of α–Keto Acids from the L–Glutamic Acid Amino Donor," Bull Sing. N.I. Chem. 18:127–29 (1990).
Lipkowski, A.W., et al., "Resolution of β–2–Thienylalanine Enantiomers by a Convenient Method," Polish J. of Chem. 54:2225–28 (1981).
Pugniére, M., et al., "A Recirculating Packed–Bed Reactor for Enzyme Catalysed Reactions in Two Liquid–Phase System," Biotech. Techniques 3(5):339–44 (1989).
Scott, T., et al., Concise Encyclopedia Biochemistry 1, 75–82 (2d ed. 1988).
Lipkowski, A.W., "Resolution of t–Butyloxycarbonyl–α–Phenylglycine Enantiomers by a Convenient Method," Polish Journal of Chemistry 55:1725–27 (1981).
Tan et al. "Synthesis and Study of S–furylmethylenehydrations . . . ", J. Phys. Org. Chem., 4(11), 681–8, 1991.
Meanwell et al. ". . . Preparation of C–5 Unsturated Hydantoin Derivatives", J. Org. Chem. 56, 6897–6904, 1991.

*Primary Examiner*—Jeffrey C. Mullis
*Attorney, Agent, or Firm*—Finnegan, Henderson, Farabow, Garrett & Dunner, L.L.P.

[57] ABSTRACT

Process for the biotechnological preparation of L-thienylalanines in enantiomerically pure form from 2-hydroxy-3-thienylacrylic acids, and their use.

L-Thienylalanines are prepared via the hydantoin or the azlactone route. The starting substances used for the biotransformation are 2-hydroxy-3-thienylacrylic acids. The innovative step consists in the transamination of the enol form of the 2-hydroxy-3-thienylacrylic acids to give L-thienylalanines with the aid of biotransformation. The transaminiation is carried out in the presence of L-aspartic acid or L-glutamic acid as amino donor.

2 Claims, No Drawings

PROCESS FOR THE BIOTECHNOLOGICAL PREPARATION OF L-THIENYLALANINES IN ENANTIOMERICALLY PURE FORM FROM 2-HYDROXY-3-THIENYLACRYLIC ACIDS AND THEIR USE

This is a division of application Ser. No. 08/099,352, filed Jul. 19, 1993 now U.S. Pat. No. 5,480,786.

L-Thienylalanines are prepared via the hydantoin or the azlactone route. 2-Hydroxy-3-thienylacrylic acids are used as starting material for the biotransformation. The innovative step consists in transaminating the enol form of the 2-hydroxy-3-thienylacrylic acids to give L-thienylalanines by means of biotransformation. The transamination is effected in the presence of L-aspartic acid or L-glutamic acid as amino donor.

Optically active, non-proteinogenic amino acids, such as, for example, L-thienylalanine, are highly important as pharmaceuticals, crop protection agents or synthesis units. Examples are L-dopa against Parkinson's Disease, alpha-methyldopa against hypertension or L-phosphinothricin as biologically active component of a herbicidal active substance.

Moreover, optically active amino acids are synthesis precursors, in particular for pharmaceuticals, such as, for example, D-phenylglycine or D-parahydroxyphenylglycine in the preparation of semisynthetic pencillins. They are used, moreover, as chiral synthesis units for other chiral fine chemicals and for incorporation into modified biologically active peptides [R. A. Sheldon, H. J. M. Zeegers, J. P. M. Houbiers and L. A. Hulshof, Chimicaoggi, 5, p. 35 (1991)].

Since the non-proteinogenic optically active amino acids cannot be obtained by fermentation or from natural sources, they have hitherto been prepared by conventional synthesis followed by racemate resolution, by asymmetric synthesis using chiral auxiliaries, or by biotransformation of chiral or prochiral precursors.

Examples of processes used for the commercial synthesis of non-proteinogenic amino acids are the following:

1. The amidase process, in which the racemic amino acid amides are cleaved by hydrolysis using an L-specific aminopeptidase [W. H. J. Boesten, U.S. Pat. No. 3,971,700 (1976)].
2. Acylase-catalyzed enantioselective hydrolysis of N-acetyl-D,L-amino acids [I. Chibata and T. Tosa, Ann. Rev. Biophys. Bioeng., 10, 197 (1981)].

The shortcoming of both processes is that the yield of the optically active reaction product is not more than 50%.

In a more advanced biotechnological process, namely the microbial hydrolysis of D,L-monosubstituted hydantoins, the chiral precursor of the amino acid can be converted into the enantiomerically pure L-amino acid with a yield of more than 50% by the presence of a racemase [Ch. Syldatk, A. Laufer, R. Müller and H. Höke in Advances Biochem. Engin. in Biotechnol. Vol. 41, A. Fiechter (Ed.), p. 29 to 75, Springer Verlag, Berlin, N.Y., London (1990)]. The shortcomings of this process are, on the one hand, that synthesis of the saturated (hydrogenated) hydantoin precursors is difficult, in particular when they contain sulfur-containing part-structures which result in inactivation of noble-metal hydrogenation catalysts and require more complicated, electrochemical reduction processes for providing the precursors (H. Hoeke, Conference Paper, Chiral '92, Manchester UK 1992). On the other hand, this process is highly complicated from the technological point of view since it is a multi-step process in which at least three enzymes are employed. The enzymes involved have different activities at certain pH values and certain temperatures, which means that process control is complicated [A. Möller, C. Syldatk, M. Schulze, F. Wagner, Enzyme Microbiol. Technol. 10, p. 618 (1988)].

A further possibility for carrying out the enantiospecific synthesis of amino acids is the transamination of prochiral alpha-keto acid precursors. This process was described mainly for the synthesis of natural amino acids, but also for non-proteinogenic amino acids [synthesis of L-leucine of alpha-ketoisocaproic acid using a Corynebacterium glutamicum strain (R. Wichmann, C. Wandrey and I. Große-Weismann, J. Appl. Microbiol. Biotechnol., 32, p. 373 (1990)].

European Patent Application 0,152,275 describes a process for the preparation of the proteinogenic amino acid phenylalanine with the aid of a genetically modified microorganism characterized by aminotransferase overproduction.

Other amino acids which are obtained by microbial or enzymatic biotransformation of the corresponding alpha-keto acids are non-proteinogenic amino acids. Examples are the process for the preparation of L-tertiary-leucine and L-phosphinothricin using a genetically modified E. coli strain (EP 0,248,357), and the transamination of a series of alpha-keto acids using an isolated aspartate aminotransferase from E. coli and glutamic acid as amino donor [J. E. Baldwin and S. C. Ng, Bull. Sing. N. I. Chem., 18, p. 127 (1990)].

The following processes, which are restricted to the L-3-(2-thienyl)alanine basic structural type, have been described to date for the synthesis of the optically active, non-proteinogenic thienylalanines:

a) Traditional racemate resolution by crystallization of diastereomeric salts [A. W. Lipkowski and G. Flouret, Pol. J. Chem., 54, p. 2225 (1980)];

b) Enantioselective hydrolysis of lower alkyl esters by means of alpha-chymotrypsin [M. Pugniere, L. G. Barry and A. Previero, Biotechnol. Techniques, 3, p. 339 (1989)];

c) Racemate resolution of the corresponding amino acid amide with an aminopeptidase by the process of R. A. Sheldon (in "Chiral Synthesis", Proceedings of the Chiral Synthesis Workshop, Manchester, UK, 18th Apr. 1989, Conference Paper, p. 25);

d) The hydantoinase process by Ch. Syldatk et al. [Ch. Syldatk, A. Läufer, R. Miller and H. Höke in Advances Biochem. Engin. in Biotechnol. Vol. 41, A. Fiechter (Ed.), p. 29 to 75, Springer Verlag, Berlin, N.Y., London (1990)] and e) Enzymatic addition of ammonia onto trans-3-(2-thienyl)acrylic acid (WO 8912-688).

The processes mentioned above under a) to c), like all racemic processes, have the abovementioned shortcoming in terms of yield. While the shortcoming of the hydantoinase process for the synthesis of thienylalanine consists mainly in the problematic accessibility of the 5-thienylmethylhydantoin required, the concentration of substrate in the last-mentioned process is low at only approximately 3 g/l and, on the 100 milligram scale, the process provides the desired amino acid L-3-(2-thienyl) alanine in a yield of 47.9 mg (43%). The process is not suitable for syntheses on an industrial scale.

Surprisingly, a process for the preparation of L-thienylalanines in enantiomerically pure form from 2-hydroxy-3-thienylacrylic acids has now been found, in which the enol form of the 2-hydroxy-3-thienylacrylic acids is transaminated into the respective non-proteinogenic amino acid in the presence of L-aspartic acid or L-glutamic acid as amino donor.

The invention therefore relates to

1. A process for the preparation of thienylalanines of the formula I

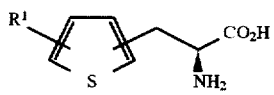

in which $R^1$ is hydrogen, a halogen radical, a nitro radical or a straight-chain or branched alkyl radical and the 2-hydroxyacrylic acid radical is in the 2- or 3-position of the thiophene ring, or the salts of these compounds, which comprises subjecting the compounds of the formula II

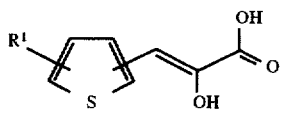

in which $R^1$ has the abovementioned meanings to biotransformation in the presence of the amino acids asparagine, glutamine, L-aspartic acid and/or L-glutamic acid and in the presence of microorganisms or enzymes with transaminase activity.

2. The use of the compounds of the formula I as units for peptide synthesis.

In the following text, the invention is described in detail and defined in the patent claims.

The term thienylalanine is used for non-proteinogenic amino acids which are composed of a substituted or unsubstituted thiophene basic structure which is linked in the 2'- or 3'-position to the alanine side chain.

The process for the synthesis of L-thienylalanines can be carried out on a bench scale (preparation of amounts <100 g) and also on an industrial scale.

Moreover, the process can be carried out continuously or batchwise. A person skilled in the art understands the term continuous process in a chemical apparatus as meaning a constant feeding of the reactants and constant discharge of the reaction products.

A person skilled in the art understands the term batchwise, or discontinuous, process as meaning a way of carrying out a reaction in which materials involved in the reaction can be added or withdrawn stepwise.

An industrial scale is defined as the synthesis of L-thienylalanines in amounts of 100 g and more.

The thienylaldehydes of the formula I, which are used as starting material, for example 4-bromo-, 5-bromo-, 3-methyl-, 5-methyl- or 5-nitro-thiophenealdehydes, are either commercially available or can be prepared from commercially available precursors by a person skilled in the art by generally known synthesis methods.

L-Thienylalanines can be prepared via the following reaction steps, all of which are of the prior art, with the exception of the biotransformation of the enol form in question:

a) the hydantoin route (diagram 1) or b) the azlactone route (diagram 2).

The synthesis route shown in diagram 1 is illustrated in greater detail in diagram 3 with the aid of L-3-(2-thienyl) alanine synthesis (2A).

Diagram 1:

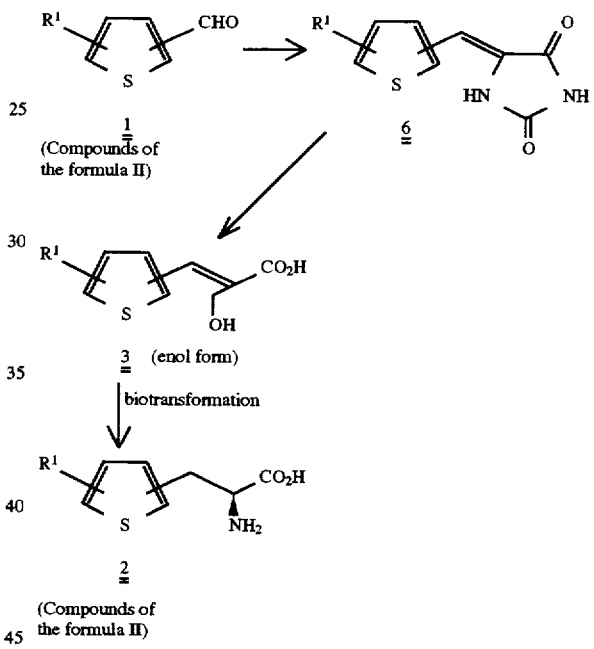

Diagram 2:

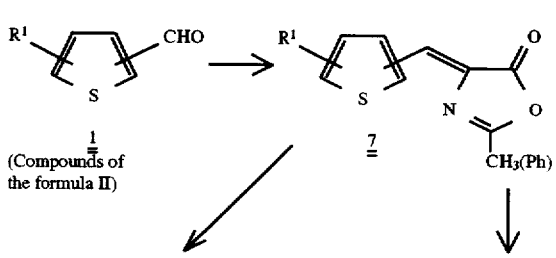

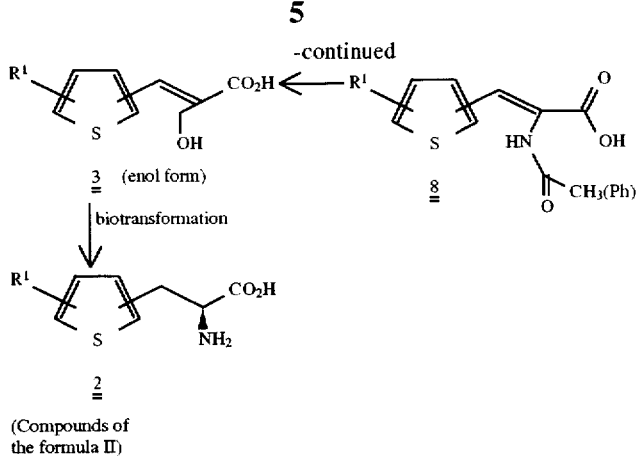

3 (enol form)

8

(Compounds of the formula II)

Diagram 3:

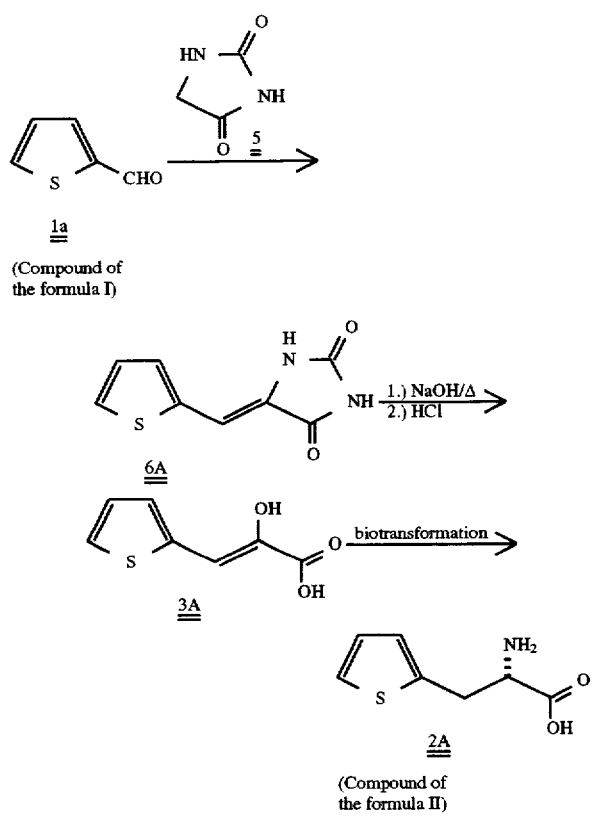

1a
(Compound of the formula I)

6A

3A 2A
(Compound of the formula II)

As shown in the diagrams, the 2-hydroxy-3-thienylacrylic acids (3) are obtained by hydrolytic ring opening of the corresponding heterocyclic precursors (6) or (7). The hydantoin derivatives (6) can be obtained by processes known from the literature, for example by aldol condensation using unsubstituted hydantoin (5), from the amino acids using metal cyanates or from the 3-thienyl-substituted propanals using metal cyanides and urea in a Bucherer-Berg synthesis (E. Ware, "The Chemistry of Hydantoins", in Chem. Rev., R. L. Shriner (Ed.), Vol. 46, 403–470, The Williams & Wilkins Comp., Baltimore (1950)). The synthesis of the enolcarboxylic acids (3) from the hydantoin derivatives (6) was hitherto not described in the literature and, surprisingly, proceeds in high yields by simply heating hydantoins in aqueous bases up to the boiling point of the aqeuous solution.

The synthesis of the enolcarboxylic acids (3; see diagram 2)) from the azlactone derivatives (7) can be carried out, in principle, in close analogy to the processes known from the literature by heating the substances in aqueous acids or bases (J. P. Greenstein and M. Winitz, "Chemistry of the Amino Acids", Wiley, N.Y. 1961). Hydrolysis of the azlactones (7) can also be carried out in two steps (diagram 2) via the 2-benzoylamidoacrylates or 2-acetylamidoacrylates (8) as intermediates (B. F. Crowe and F. F. Nord, J. Org. Chem. 15, 1177 (1950)).

A series of other syntheses for alpha-ketocarboxylic acids, which can, in principle, also be used for the preparation of the intermediates of the formula (3) can be found in the review article by A. J. L. Cooper, J. Z. Ginos, A. Meister, Chem. Rev. 83, 321 (1983). However, the synthesis routes given in diagrams 1–3 are to be preferred for realization on an industrial scale with regard to yields and good accessibility of the chemicals required and for economic reasons.

The precursors in the enol form (3) which have been prepared by various synthesis routes can be reacted by the process according to the invention in the sense of a transamination reaction to give the amino acids (2). The spectroscopic findings (infrared spectroscopy, nuclear resonance spectroscopy) demonstrate within the detection range of these analytical techniques that exclusively the tautomeric compounds (3), which have the enol structure shown in diagrams 1–3, are present in organic and aqueous solvents and in wide pH ranges (pH 1–14), in particular under the pH conditions of the biotransformation. This finding is in contrast to information found in the literature, for example for the compound 3A (2-thienyl radical and $R^1=H$), which has been described in the literature by the corresponding keto acid structural formula (4A). (L. Horner and E.-O. Renth, Liebigs Ann. Chem., 703,37 (1967). In contrast, the corresponding enol structures of esters of the relevant 2-hydroxy-3-thienylacrylic acids and of the corresponding 2-mercapto compounds have been described in the literature as stable tautomeric forms (2-thienylthiopyruvic acid in: B. F. Crowe and F. F. Nord, J. Org. Chem. 15,81 (1950); Esters in: A. M. Stock, W. E. Donahue and E. D. Amstutz, J. Org. Chem. 23, 1840 (1958)). In general, substantial amounts of aryl-substituted beta-pyruvic acids of the general formula aryl-CH(2)—C(=O)CO(2)H are present in the tautomeric enol form only in a very basic medium. Under physiological pH conditions, the enol content is very poor (A. J. L. Cooper, J. Z. Ginos and A. Meister, Chem. Rev. 83,321 (1983)). For example, the sodium salt of phenylpyruvic acid is present almost exclusively in the keto acid form, according to NMR spectrum (The Aldrich Library of NMR-Spectra, 2nd Edition, Vol. 2, 143C, p. 2).

Substances which can be employed according to the invention for the biotransformation of the enolcarboxylic acids (3) into the amino acids (2) are all enzymes from animals, plants, microorganisms or animal organs, such as, for example, pigs' hearts, which are capable of converting alpha-keto acids into natural L-amino acids by transamination.

However, the process is preferably carried out using microorganisms which have a transaminase, such as, for example, microorganisms from the genera Paracoccus, Alkaligenes, Rhizobium, Pseudomonas, Serratia, Agrobacterium, Streptomyces or Enterobacterium.

Species from these preferred genera which can be used are, for example: *Alcaligenes faecalis* DSM 4115, *Alcaligenes denitrificans* DSM 4114, *Pseudomonas paucimobilis* DSM 4120, *Pseudomonas spec.* DSM 4119, *Serratia plymuthica* DSM 4116, *Agrobacterium tumefaciens*, *Escherichia coli* DH1, *Enterobacter agglomerans* DSM 4122, *Enterobacter spec.* DSM 4121, *Streptomyces hygroscopicus*, *Streptomyces viridochromogenes* or the soil isolates DSM 4113, DSM 4117 and DSM 4118.

*Escherichia coli* ATCC 11303 and *Paracoccus denitrificans* DSM 65 are particularly preferred.

The microorganisms can be employed in the form of a pure or mixed culture.

These microorganisms are available at the Deutsche Sammlung für Mikroorganismen und Zellkulturen [German Collection of Microorganisms and Tissue Cultures] (DSM), Mascheroder Weg 1B, 3300 Braunschweig, Germany, or from the American Type Culture Collection (ATCC); 12301 Parklawn Drive; Rockville, Md. 20852; USA.

The enzyme activities of the microorganisms can be increased by selecting strains which are resistant to the product of the biotransformation according to the invention, 3-(2-thienyl)alanine (2A), or which utilize this compound as the sole nitrogen source.

This is a generally customary process for the selection of good producers of the amino acid L-phenylalanine and is described, for example, in Japanese Patent Application JP 9071-698.

It is also possible to use selection and mutation, in a manner known per se, in the presence of increasing amounts of the 2-hydroxy-3-thienylacrylic acids or salts thereof in the culture media for further work for selecting microorganisms which carry out the biotransformation in higher yields because they are adapted to the substrate.

Particularly high yields are obtained when mutants of microorganisms are employed which have been genetically engineered. A microorganism which is particularly preferably employed is the bacterial strain *E. coli* ATCC 11303, which was additionally transformed with a plasmid containing the tyrB gene or, additionally, the aspA gene, the tyrB gene encoding aromatic transaminase and the aspA gene encoding aspartase in *E. coli*. *E. coli* ATCC 11303 bacteria which have been transformed in such a manner can be produced, for example, by the method described in German Patent Applications P 3631829.9 and P 3713755.2, respectively, and EP 248,357.

The microorganisms are grown advantageously under favorable temperature and aeration conditions in a culture medium which is optimal for their growth until a dry weight of approximately 4–60 g/l of culture liquid is reached. The conditions which are most favorable for the culture organism in question are either known to a person skilled in the art or can be determined in simple preliminary trials. The cells are then used for biotransformation of the 2-hydroxy-3-thienylacrylic acids, either in the liquid medium or separated from the liquid medium. The biotransformation can be carried out using whole cells or else digested cells, customary work-up methods being employed.

The biotransformation can also be carried out using cell extracts, isolated complete proteins and purified transaminases. However, it is preferably carried out using intact cells in order to facilitate the procedure. However, it may also be advantageous to isolate the transaminases since the enzyme is longer lived and better process control is possible. Examples can be found, for example, in S.C. Ng and J. Baldwin, Bull. Sing. N. I. Chem. 18, 127 (1990), who describe an aspartate transaminase (AST) from *E. coli* (I. G. Fotheringham, S. A. Dacey, P. P. Taylor, T. G. Smith, M. G. Hunter, M. G. Finlay, S.B. Primrose, D. M. Parker and R. M. Edwards, Biochem. J., 234, 593 (1986)) for synthesizing a series of L-alpha-amino acids from alpha-keto acids. It is furthermore possible to employ the microorganisms or the enzymes in immobilized form. Methods which are suitable for the immobilization are known methods, advantageously those described in German Offenlegungsschriften 3,237,341 and 3,243,591.

Eupergit C, VA epoxy, silica gels, for example Grace XWP 250 UMP, XWP 300 MP, XWP 350 MP, XWP 1000 MP, XWP 1500 UMP, XWP 350 LP or XWP 350 HP, are preferably used as supports for the immobilied enzymes, particularly preferably XWP 500 MP.

The immobilized enzyme or the non-immobilized enzyme, can in each case be employed for the continuous process or the batch process. The immobilized enzyme is preferably used in the batch process.

In the preferred embodiment, the microorganisms or the isolated, or immobilized, enzyme are suspended in a physiological buffer with an addition of a 2-hydroxy-3-thienylacrylic acid (3) and of the amino group donor. Depending on the amount of microorganisms, the enzymatic activity added to the batch can be adjusted within wide limits. It is advantageously between 10 and 30,000 µmol/min l. The batch preferably contains an amount of cells with an enzyme activity of 10,000 to 20,000 µmol/min l.

Amino group donors which can be used are asparagine, glutamine, aspartic acid and/or glutamic acid, in each case in the L form, or fumarate or fumaric acid in combination with ammonium ions or urea, but the process is preferably carried out using L-aspartic acid and L-glutamic acid, particularly preferably L-aspartic acid. These precursors are employed in the form of their free acids or suitable salts (depending on the medium) in at least equimolar amounts or in excess relative to the substrate (3). Ratios of 1:1 to 5:1, advantageously 1:1 to 2:1, have proven themselves.

When salts are employed, natural ions are selected which have a negligible effect on the enzyme activity. These are preferably sodium, potassium and ammonium salts.

The reactants can be added to the batch in the form of a solution in water, solvents which are miscible with water, preferably pure methanol or methanol which has been diluted with water in any ratio desired, or by adding the solid substances at the same time. However, a batchwise or continuous addition in amounts of 0.5–10%, in particular 2–5%, in each case based on the batch weight, over a period of 0.5–24 hours, preferably 8–16 hours, is preferred. The process is advantageously carried out at a pH between 5 and 9, in particular between 7 and 8.5. Moreover, it is expedient to carry out the biotransformation in a temperature range of 10°–65° C., in particular 30°–45° C. At lower temperatures, the biotransformation proceeds increasingly more slowly, while higher temperatures lead to progressive deactivation of the enzyme.

It is not necessary to permeabilize the microorganisms before or during the biotransformation. High reaction rates and yields are achieved in particular when the batch is incubated with the microorganism or with the enzyme under the exclusion of atmospheric oxygen. Inert gases, such as nitrogen, and also rare gases, such as, for example, argon, are suitable.

When carrying out the transamination by means of immobilized enzymes, the reaction solution is reacted batchwise or continuously with the catalyst. The concentration of 2-hydroxy-3-(2-thienyl)acrylic acid in the reaction solution is 0.5–5%, preferably 1–2%. The concentration of the donor amino acid corresponds to the batch with integers. The reaction solution (introduced cooled to 4° C.) is reacted at 10°–65° C., preferably 30°–45° C. The immobilized enzyme can be employed in a stirred reactor and also in a column reactor, preferably using the fixed-bed process. In the latter process, the reaction solution is pumped through the column at a rate of 0.1–20 ml, in particular 0.1–0.5 ml per minute, the enzyme being immobilized.

The non-proteinogenic L-thienylalanines can be used as units for the synthesis of peptides, preferably for the synthesis of bradykinin or peptides related to bradykinin.

Bradykinin has the amino acid sequence Arg-Pro-Pro-Gly-Phe-Ser-Pro-Phe-Arg and belongs to the kinins, a group of plasma hormones. A bradykinin-related peptide is lysyl-bradykinin which, like bradykinin, has a hypotensive action, stimulates the contraction of specific muscles and has pain-stimulating action (Concise Encyclopedia Biochemistry, 2nd Edition, Thomas Scott and Mary Eagleson, Walter de Gruyter, Berlin, N.Y. 1988, p. 75).

Peptides of the formula A-B-C-E-F-K-(D)-Tic-G-M-F-I in which A is hydrogen, alkyl, alkanoyl, alkoxycarbonyl, alkylsulfonyl, cycloalkyl, aryl, arylsulfonyl, heteroaryl or an amino acid, each of which can optionally be substituted, B is a basic amino acid, C is a di- or tripeptide, E is the radical of an aromatic amino acid, the F radicals independently of one another are amino acids which are optionally substituted in the side chain, F' has the same definition as F or is —NH—(CH$_2$)$_2$—, or can, if appropriate, be a direct bond, I is —OH, —NH$_2$ or —NHC$_2$H$_5$ and K is a radical of the formula —NH—(CH$_2$)$_{1-4}$—CO— or a direct bond, are bradykinin antagonists. They can be used in therapy for all pathological conditions which are mediated, triggered or enhanced by bradykinin and bradykinin-related peptides.

The peptides are prepared by generally known methods of peptide chemistry, see, for example, Houben-Weyl, Methoden der organischen Chemie [Methods in Organic Chemistry], Volume 15/2, preferably by means of solid phase synthesis, such as, for example, as described by B. Merrifield, J. Am. Chem. Soc. 85, 2149 (1963) or R. C. Sheppard, Int. J. Peptide Protein Res. 21, 118 (1983), or by equivalent known methods. Groups which are used as α-amino protective groups are urethane protective groups, such as, for example, the tert.-butyloxycarbonyl-(Boc) or fluorenylmethyloxycarbonyl(Fmoc) protective group. If specific peptides are required for preventing secondary reactions or for the synthesis, the functional groups in the side chain of amino acids are additionally protected by suitable protective groups (see, for example, B. T. W. Greene, "Protective Groups in Organic Synthesis").

The examples which follow are intended to illustrate the invention in greater detail.

EXAMPLE 1

Synthesis of 2-hydroxy-3-(2-thienyl)acrylic Acid (3A)

Synthesis via the azlactone route

Azlactone synthesis and hydrolysis to give 2-hydroxy-3-(2-thienyl)acrylic acid (3A)

420 g (4.9 mol) of anhydrous sodium acetate and 500 g of acetylglycine are dissolved or suspended in 1300 g of acetic anhydride, and 719 g of thiophene-2-aldehyde are added. The batch is heated to the boil under inert gas and refluxed for 1.5 hours. The batch is subsequently cooled in an ice-bath, and the product which has precipitated is filtered off with suction. This is washed four times using 300 ml of ice-water, and the residue is dried in a vacuum shelf dryer at 50° C. Precipitated product from the combined filtrates is treated in the same manner.

Total azlactone (7A) yield: 730 g, 88%.

Melting point: 137°–140° C. $^1$H NMR (100 MHz, chemical shift in ppm, DMSO-d$_6$): 8.2–6.8 (several m, 4H, aromatic H, =CH); 4.60 (s, 3H, CH$_3$)

193 g (1 mol) of the resulting azlactone (7A) are introduced into 1.5 l of boiling hydrochloric acid. After 30 minutes under reflux, most of the educt is dissolved. The mixture is filtered while hot and washed with a little water. The reddish-brown residue is composed of the aminoacetyl acid 8 A (55 g, 26%). The filtrate is cooled to 0° C. while stirring. 2-Hydroxy-3-(2-thienyl)acrylic acid (3A) and more aminoacetyl acid 2-acetamidoacrylic acid 8A precipitate. The mixture is refiltered with suction and washed with a little cold water. The residue remaining on the frit is digested several times with ether and filtered off with suction. What remains on the frit is aminoacetylacrylic acid (8A; 50 g, 25%).

2-Hydroxy-3-(2-thienyl)acrylic acid (3 A) is isolated from the ether phase after evaporation on a rotary evaporator and drying (46 g, 27%).

Melting point: 166°–168° C. $^1$H NMR (100 MHz, chemical shift in ppm, DMSO-d$_6$): 7.52; 7.25;, 7.02 (3dd, 3 H, aromatic H) 6.75 (s, 1 H, =CH)

Alternative route: Reaction of the azlacttone (7 A) after isolation of 2-aminoacetylacrylic acid (8 A) to give 2-hydroxy-3-(2-thienyl)acrylic acid (3 A).

96.5 g of the azlactone (7 A) are dissolved in 500 ml of dioxane and 11 ml of water. HCl gas is subsequently passed in. Aminoacetylacrylic acid starts to crystallize out and is in the form of a thick suspension when the reaction has ended 40 minutes later. 1 l of diethyl ether is added with stirring, and the hydrogen chloride which is dissolved is expelled by passing in nitrogen. The product is filtered off with suction, washed thoroughly with ether and freed in vacuo from remains of solvent. Yield of aminoacetylacrylic acid: 99.5 g, 94% of theory.

Melting point: 232°–235° C. $^1$H NMR (100 MHz, chemical shift in ppm, DMSO-d$_6$): 9.25 (s, 1 H, NH) 7.75 (d, 1 H, aromatic H) 7.70 (s, 1 H, =CH) 7.50 (d, 1 H, aromatic H) 7.10 (dd, 1 H)

The hydrolysis with hydrochloric acid which is subsequently carried out is effected as described above; yield of 2-hydroxy-3-(2-thienyl)acrylic acid 70–75%.

Synthesis via the hydantoin route

Reaction of 5-(2-thienyliden) hydantoin (6 A) with sodium hydroxide solution to give 2-hydroxy-3-(2-thienyl) acrylic acid (3A)

1.2 l of 5N NaOH are heated at the boil while stirring and passing in inert gas. 77.7 g (0.4 mol) of the hydantoin (6 A) are introduced, and the mixture is left on the reflux for 60 minutes. The mixture is subsequently cooled in an ice-bath and slowly treated with 500 ml of concentrated hydrochloric acid. Some of the product (3 A) precipitates directly, the remainder can be extracted from the aqueous filtrate using ether. Total yield of dried product 3 A: 66.9% of theory.

Analytical data of the hydantoin (6A):

Melting points 263°–264° C. $^1$H NMR (100 MHz, chemical shift in ppm, DMSO-d$_6$): 7.70; 7.60; 7.18 (3 dd, 3 H, aromatic H) 6.59 (s, 1 H, =C—H)

EXAMPLE 2

Synthesis of 2-hydroxy-3-(3-thienyl)acrylic Acid (3B)

The synthesis is as described in Example 1.
Analytical data:

a) 5-(3-thienyliden)-2-methyl-3-oxazolin-4-one (7B): Melting point: 112°–116° C. $^1$H NMR (100 MHz, chemical shift in ppm, DMSO-$d_6$): 8.34; 7.90; 7.68 (3 dd, 3 H, aromatic H) 7.28 (s, 1 H, =CH) 2.37 (s, 1H, —CH$_3$)

b) 2-Aminoacetyl-3-(3-thienyl)acrylic acid (8 B): Melting point: 205° C. $^1$H NMR (100 MHz, chemical shift in ppm, DMSO-$d_6$): 7.93; 7.60; 7.41 (3 dd, 3 H, aromatic H) 7.33 (s, 1 H, =CH) 2.00 (s, 1 H, CH$_3$ N-AC)

c) 5-(3-thienyliden) hydantoin (6 B): Melting point: 270° C. $^1$H NMR (100 MHz, chemical shift in ppm, DMSO-$d_6$): 7.95 (m, 1 H, aromatic H) 7.68–7.42 (4dd, 2 H, aromatic H) 6.50 (s, 1 H, =CH)

d) Hydroxy-3-(3-thienyl)acrylic acid (3 B): Melting point: 178°–180° C. $^1$H NMR (100 MHz, chemical shift in ppm, DMSO-$d_6$): 9.10 (s, 1 H, COOH) 7.75; 7.45 (2 m, 3 H, aromatic H) 6.50 (s, 1 H, =CH)

EXAMPLE 3

Synthesis of 2-hydroxy-3-(4-bromo-3-thienyl) acrylic Acid (3C)

The synthesis is as described in Example 1.
Analytical data:

a) 5-(4-Bromo-2-thienyliden)-2-methyl-3-oxazolin-4-one (7C): Melting point: 142v–145° C. $^1$H NMR (100 MHz, chemical shift in ppm, DMSO-$d_6$); 8.05; 7.75; 7.54 (per s, per 1 H, aromatic H, =CH) 2.37 (s, 3 H, CH$_3$)

b) 2-Aminoacetyl-3-(4-bromo-2-thienyl)acrylic acid (8C): Melting point 213°–215° C. $^1$H NMR (100 MHz, chemical shift in ppm, DMSO-$d_6$); 7.30 (s, br, 1 H, NH) 7.80; 7.65; 7.5 (per s, per 1 H, aromatic H, =CH) 2.00 (s, 3 H, CH$_3$N-Ac)

c) 5-(4-Bromo-2-thienyl)hydantoin (6C): Melting point 220°–221° C. $^1$H NMR (100 MHz, chemical shift in ppm, DMSO-d6): 11.35; 10.52 (2 s, 2 H, NH) 7.77; 7.65 (2 "s", 2 H, aromatic H) 6.48 (s, 1 H, =CH)

d) 2-Hydroxy-3-(4-bromo-2-thienyl)acrylic acid (3C): Melting point 194°–195° C. $^1$H NMR (100 MHz, chemical shift in ppm, DMSO-$d_6$): 9.30 (s, br, 1 H, COOH) 7.63; 7.25 (per s |br|, per 1 H, aromatic H) 6.75 (s, 1 H, =CH)

EXAMPLE 4

Synthesis of 2-hydroxy-3-(5-bromo-2-thienyl) acrylic Acid (3D)

The synthesis is as described in Example 1.
Analytical data:

a) 5-(5-Bromo-2-thienyliden)-2-methyl-3-oxazolin-4-one (7D): Melting point 192° C. $^1$H NMR (100 MHz, chemical shift in ppm, DMSO-$d_6$): 7.55 (d, 1 H, aromatic H) 7.50 (s, 1 H, CH) 7.35 (d, 1 H, aromatic H) 2.35 (s, 3 H, CH$_3$)

b) 2-Aminoacetyl-3-(5-bromo-2-thienyl)acrylic acid (8D): Melting point 221°–222° C. $^1$H NMR (100 MHz, chemical shift in ppm, DMSO-$d_6$) : 9.30 (s, 1 H, NH) 7.75 (s |br|, 1 H, =CH) 7.35 (d, 1 H, aromatic H) 7.25 (d, 1 H, aromatic H) 2.03 (s, 3 H, N-Ac)

c) 5-(5-Bromo-2-thienyliden)hydantoin(6 D): Melting point 235°–236° C. $^1$H NMR (100 MHz, chemical shift in ppm, DMSO-$d_6$): 11.3; 10.4 (2 s, 2 H, NH) 7.42; 7.30 (2 d, 2 H, aromatic H) 6.52 (s, 1 H, =CH)

d) 2-Hydroxy-3-(5-bromo-2-thienyl)acrylic acid (3 D): Melting point 56°–58° C. $^1$H NMR (100 MHz, chemical shift in ppm, DMSO-$d_6$): 9.40 (s |br|, 1 H, COOH) 7.05 (d, 1 H, aromatic H) 6.75 (d |split|, 1 H, aromatic H) 6.70 (s, 1 H, =CH)

EXAMPLE 5

Synthesis of 2-hydroxy-3-(3-methyl-2-thienyl) acrylic Acid (3E)

The synthesis is as described in Example 1.

a) 5-(3-Methyl-2-thienyliden) -2-methyl-3-oxazolin-4-one (7 E): Melting point 145°–146° C. $^1$H NMR (100 MHz, chemical shift in ppm, DMSO-$d_6$): 7.90 (d, 1 H, aromatic H) 7.35 (s, 1 H, =CH) 7.03 (d, 1 H, aromatic H) 2.40; 2.25 (2 s, 6 H, CH$_3$)

b) 2-Aminoacetyl-3-(3-methyl-2-thienyl)acrylic acid (8 E): Melting point 231°–232° C. $^1$H NMR (100 MHz, chemical shift in ppm, DMSO-=$d_6$): 9.25 (s, br, 1 H, NH) 7.65 (d, 1 H, aromatic H) 7.60 (s, 1 H, =CH) 7.00 (d, 1 H, aromatic H)

c) 5-(3-Methyl-2-thienyliden)hydantoin (6 E): Melting point 212°–214° C. $^1$H NMR (100 MHz, chemical shift in ppm, DMSO-$d_6$): 11.23; 10.02 (2 d, 2 H, NH) 7.65; 7.00 (2 d, 2 H, aromatic H) 6.60 (s, 1 H, =CH) 2.29 (s, 3 H, CH$_3$)

d) 2-Hydroxy-3-(3-methyl-2-thienyl)acrylic acid (3 E): Melting point 184°–185° C. $^1$H NMR (100 MHz, chemical shift in ppm, DMSO-$d_6$): 7.45 (d, 1 H, aromatic H) 6.90 (d, 1 H, aromatic H) 6.70 (s, 1 H, =CH) 2.23 (s, 3 H, CH$_3$)

EXAMPLE 6

Synthesis of 2-hydroxy-3-(5-methyl-2-thienyl) acrylic Acid (3 F)

The synthesis is as described in Example 1.
Analytical data:

a) 5-(5-Methyl-2-thienyliden) -2-methyl-3-oxazolin-4-one (7 F): Melting point 280° C. (decomposition) $^1$H NMR (100 MHz, chemical shift in ppm, DMSO-$d_6$): 7.57 (d, 1 H, aromatic H) 7.48 (s, 1 H, =CH) 6.93 (d, split, 1 H, aromatic H) 2.50; 2.32 (2 s, per 3 H, CH$_3$)

b) 2-Aminoacetyl-3-(5-methyl-2-thienyl)acrylic acid (8 F): Melting point 257° C. $^1$H NMR (100 MHz, chemical shift in ppm, DMSO-$d_6$); 9.20 (s, br, 1 H, NH) 7.60 (s, 1 H, =CH) 7.30 (d, 1 H, aromatic H) 6.80 (d split, 1 H, aromatic H) 2.00 (s, 3 H, N-Ac)

c) 5-(5-Methyl-2-thienyliden)hydantoin (6 F): Melting point 263°–264° C. $^1$H NMR (100 MHz, chemical shift in ppm, DMSO-$d_6$): 11.2; 10.22 (2 s, 2 H, NH) 7.40; 6.85 (2 d, 2 H, aromatic H) 6.45 (s, 1 H, =CH) 2.45 (s, 3 H, —CH)

d) 2-Hydroxy-3-(5-methyl-2-thienyl)acrylic acid (3 F): Melting point 184°–185° C. $^1$H NMR (100 MHz, chemical shift in ppm, DMSO-$d_6$) : 9.3 (s, br, 1 H, COOH) 7.05 (d, 1 H, aromatic H) 6.7 (d, split, 1 H, aromatic H) 6.68 (s, 1 H, =CH) 2.43 (s, 3 H, CH$_3$)

EXAMPLE 7

Synthesis of 2-hydroxy-3-(5-nitro-2-thienyl)acrylic Acid (3G):

The synthesis is as in Example 1.

a) 5-(5-Nitro-2-thienyliden)-2-methyl-3-oxazolin-4-one (7 G): Melting point >300° C. $^1$H NMR (100 MHz, chemical shift in ppm, DMSO-$d_6$): 8.05 (d, 1 H, aromatic H) 7.68 (s, 1 H, =CH) 7.48 (d, 1 H, aromatic H) 2.16; 2.05 (2 S, 3 H, CH$_3$)

b) 2-Aminoacetyl-3-(5-nitro-2-thienyl)acrylic acid (8 G): Melting point 220° C. $^1$H NMR (100 MHz, chemical shift in ppm, DMSO-$d_6$): 8.15 (d, 1 H, aromatic H) 7.75 (s, 1 H, =CH) 7.60 (d, 1 H, aromatic H) 2.06 (s, 1 H, CH$_3$, N-Ac)

c) 5-(5-Nitro-2-thienyliden)hydantoin (6 G): Melting point: not determined $^1$H NMR (100 MHz, chemical shift in ppm, DMSO-$d_6$): not determined d) 2-Hydroxy-3-(5-nitro-2-thienyl)acrylic acid (3 G): Melting point 192°–193° C. $^1$H NMR (100 MHz, chemical shift in ppm, DMSO-$d_6$): 8.06 (d, 1 H, aromatic H) 7.34 (d, 1 H, aromatic H) 6.87 (s, 1 H, =CH)

EXAMPLE 8

Synthesis of L-3-(2-thienyl)alanine (2A)

30 g of 2-hydroxy-3-(2-thienyl)acrylic acid, 29 g of L-aspartate and 40 mg of pyridoxal phosphate were dissolved in 700 ml of distilled water, and the pH was brought to 8 using NaOH (solution 1). The resulting solution was cooled to 4° C. In a 1 l reactor, 100 ml of a suspension of E. coli Z 1196/6 (corresponds to approximately 6 g of dry matter or 3000 U transaminase activity) were introduced together with 200 ml of distilled water (solution 2). The pH of this suspension was brought to 8, and the mixture brought to 40° C. N$_2$ was passed in at a rate of 0.1 vvm. Solution 1 was metered into this suspension with stirring in the course of 16 hours. The pH was kept constant by means of NaOH/H$_2$SO$_4$. After 24 hours, the concentration of L-3-(2-thienyl)alanine was 24.6 g/l (82% yield). The reaction mixture was centrifuged (15 minutes, 8000 g), the supernatant was brought to pH 1.5, 5 g of active charcoal were added, and the suspension was stirred for 30 minutes at 70° C. It was subsequently cooled to 4° C., and the precipitate was filtered off. The filtrate was brought to pH 12 using NaOH. The solution was applied to a column packed with 1 l of Dowex 1×2 (Cl). It was rinsed with 2 l of water (brought to pH 9 using ammonia). L-3-(2-thienyl)alanine was eluted using 4 l of 0.105% acetic acid. The eluate was concentrated in vacuo to 300 ml, and the resulting concentrate was lyophilized.

Yield of L-3-(2-thienyl)alanine: 17.8 g. HPLC: Purity >98%, D enantiomer <0.2% Optical rotation: –30.1° (c=1, H$_2$O)

$^1$H NMR (300 MHz, in D$_2$O, chemical shift in ppm): 7.26 (d, 1 H, aromatic H) 6.88 (m, 2 H, aromatic H) 3.87 ("t", 1 H, =CH) 3.35 (m, 2 H, CH$_2$)

$^{13}$C NMR (75 MHz, in D$_2$O, chemical shift in ppm): 174 (COOH) 136, 128, 128, 126 (aromatic) 56 (=CH) 30 (CH$_2$)

EXAMPLE 9

Synthesis of L-3-(3-thienyl)alanine (2B)

The procedure was largely as in Example 8. However, solution 1 contained only 20 g of hydroxy-3-(3-thienyl) acrylic acid and 19 g of L-aspartate. The product concentration was 11.5 g/l (58%) after the reaction. After ion-exchange chromatography, 7.9 g (40%) of L-3-(3-thienyl) alanine (2B) were obtained.

HPLC: Purity >90%, D enantiomer <0.2% Optical rotation: –38.9° (C=1, H$_2$O)

$^1$H NMR (300 MHz, in D$_2$O, chemical shift in ppm): 7.38; 7.18; 6.97 (3 s, br, 3 H, aromatic H) 3.88 ("t", 1 H, =CH) 3.16 (m, 2 H, CH$_2$)

EXAMPLE 10

Synthesis of L-3-(4-bromo-2-thienyl)alanine (2C)

The reaction was carried out analogously to Example 8. However, this was done on a smaller scale, and the isolation step was modified. Solution 1: 750 mg of (3C), 720 mg of L-aspartate, 4 mg of pyridoxal phosphate, and distilled water to 35 ml. Solution 2: 5 ml of cell suspension+10 ml of distilled water. After a reaction time of 6 hours, 60 mg of L-3-(4-bromo-2-thienyl)alanine had been formed. After the cells had been separated off and the mixture decolorized using active charcoal, the solution was rendered neutral, and the volume was reduced in vacuo to 10 ml. The mixture was purified by means of preparative HPLC on a Nucleosil C$_{18}$ column (10 cm×40×250 mm); flow rate 20 ml/min$^{-1}$; eluent A: H$_2$O, eluent B: acetonitrile; detection at 254 nm. Gradient 0t of B to 20% of B in 80 minutes, subsequently to 50% of B in 60 minutes. The fractions containing (2C) were combined and concentrated in vacuo to give 10 ml of aqueous residue. This solution was lyophilized. Yield 70 mg (10%) of (2C)).

HPLC: Purity >95%, D enantiomer <0.2% Optical rotation: –29.3° (c=1, H$_2$O)

$^1$H NMR: (300 MHz, in D$_2$O, chemical shift in ppm): 7.40; 7.00 (2 s, 2 H, aromatic H) 4.00 ("t", 1 H, =CH) 3.42 (m, 2 H, CH$_2$)

$^{13}$C NMR: (75 MHz, in D$_2$O, chemical shift in ppm): 173 (COOH) 138, 130, 124, 109 (aromatic) 56 (=CH) 30 (CH$_2$)

EXAMPLE 11

Synthesis of L-3-(5-bromo-2-thienyl)alanine (2D)

The reaction was carried out analogously to Example 10. However, solution 1 was composed as follows: solution 1: 1 g of 2-hydroxy-3-(bromo-2-thienyl)acrylic acid, 0.97 g of L-aspartate, 4 mg of pyridoxal phosphate, and H$_2$O to 35 ml. Solution 2: 5 ml of cell suspension+10 ml of distilled water. After a reaction time of 6 hours, 43 mg (4.3%) of product were detected. Preparative HPLC (Example 10) gave 27 mg (2.7%) of L-3-(5-bromo-2-thienyl)alanine.

HPLC: Purity >85% D enantiomer <0.2%

$^1$H NMR: (300 MHz, in D$_2$O, chemical shift in ppm): 7.50–6.95 (2 m, 2 H, aromatic H) 3.85 (m, 1 H, =CH) 3.38 (m, 2 H, CH$_2$)

$^{13}$C NMR: (75 MHz, in D$_2$O, chemical shift in ppm): 133; 132; 130; 128 (aromatic) 60 (=CH) 23 (CH$_2$)

EXAMPLE 12

Synthesis of L-3-(3-methyl-2-thienyl)alanine (2E)

The reaction was carried out analogously to Example 10. However, solution 1 is composed as follows: solution 1: 300 mg of 2-hydroxy-3-(5-methyl-2-thienyl)acrylic acid, 290 mg of L-aspartate, 4 mg of pyridoxal phosphate, and H$_2$O to 35 ml. Solution 2: 5 ml of cell suspension+10 ml of distilled water. After a reaction time of 6 hours, 210 mg (70%) of product were detected. Preparative HPLC (Example 10) gave 184 mg (61%) of L-3-(3-methyl-2-thienyl)alanine.

HPLC: Purity >95%, D enantiomer <0.2% Optical rotation: −8.8° (C=1.1, 1N NaOH)

$^1$H NMR: (300 MHz, in $D_2O$, chemical shift in ppm): 7.18; 6.82 (2 d, 2 H, aromatic H) 3.78 (dd, 1 H, =CH) 3.23 (2 dd, 2 H, CH) 2.10 (s, 3 H, $CH_3$)

$^{13}$C NMR (75 MHz, in $D_2O$, chemical shift in ppm): 175 (COOH) 137; 131; 130; 124 (aromatic) 56 (=CH) 29 ($CH_2$) 13 ($CH_3$)

EXAMPLE 13

Synthesis of L-3-(5-methyl-2-thienyl)alanine (2F)

The reaction was carried out analogously to Example 10. Solution 1: 300 mg of 2-hydroxy-3-(5-methyl-2-thienyl) acrylic acid, 290 mg of L-aspartate, 4 mg of pyridoxal phosphate, and $H_2O$ to 35 ml. Solution 2: 5 ml of cell suspension+10 ml of distilled water. After a reaction time of 6 hours, 210 mg (70%) of product were detected. Preparative HPLC (Example 10) gave 150 mg (50%) of L-3-(5-methyl-2-thienyl)alanine.

HPLC: Purity >95%, D enantiomer <0.2% Optical rotation: −19.6° (C=1, $H_2O$)

$^1$H NMR: (300 MHz, in $D_2O$, chemical shift in ppm): 7.30; 6.92 (2 d, 2 H, aromatic H) 3.94 (M, 1 H, =CH) 3.40 (m, 2 H, $CH_2$) 2.20 (s, 3 H, $CH_3$)

$^{13}$C NMR (75 MHz, in $D_2O$, chemical shift in ppm): 212 (COOH) 140; 135; 134; 128 (aromatic) 59 (=CH) 32 ($CH_2$) 17 ($CH_3$)

EXAMPLE 14

Determination of the Enantiomeric Purity by Means of HPLC

Eluent: A) 12.5 mM phosphate buffer pH 7.2 B) ACN

Reagents: 1) 50 mg/ml of OPA in analytical-grade EtOH 2) 100 mg/ml of Boc-L-cystein in analytical-grade EtOH 3) 1M potassium borate buffer pH 10.4 Immediately prior to use, 10 µl of each 1) and 2) are added to 980 µl of 3). The solution is stable for approximately 48 hours at 4° C.

Derivatization: 10 µl of a suitable dilute sample are mixed with 90 µl of reagent. After 120 seconds, the sample can be injected.

Column: Grom amino-OPA (150×4.6 mm) with identical precolumn (20×4.6 mm); flow rate: 1.5 ml min$^{-1}$; detection 340 nm; gradient: 10% to 50% of B in 13 minutes.

EXAMPLE 15

Isolation and Immobilization of the Aromatic Amino Acid Amino Transferase from *E. coli* A 1196/9

Enzyme isolation:

20 g of cells (*E. coli* Z 1196/9) were suspended in 60 ml of buffer (20 mM $KHPO_4/KH_2PO_4$, 10 µM pyridoxal phosphate, 5 mM 2-mercaptoethanol, 10 mM EDTA and 12 mg of lysozyme), and the suspension was stirred at a low speed for 10 minutes at 30° C. The resulting suspension was centrifuged for 15 minutes at 4° C, and the clear supernatant was used for the subsequent work-up. First, a precipitation was carried out for 1 hour at 4° C. using 30% of ammonia sulfate, and the mixture was subsequently centrifuged for 15 minutes at 10.000 g/4° C. The precipitate was discarded, and the supernatant was subjected to a precipitation with 70% ammonium sulfate (1 h/4° C.), and the suspension was centrifuged as above. The precipitate contained most of the transaminase and was taken up in the coupling buffer (see below).

Activation of the silica gel:

10 g of support (silica gel XWP 50 MP, manufactured by Grace) were suspended in 100 ml of distilled water, and 2300 mg of aminopropyltriethoxysilane were added. The mixture was brought to pH 2.5 using HCl and heated for 2 hours at 65° C. The mixture was subsequently filtered and washed with water until neutral, and the silica gel was dried for 24 hours at 90° C. The dry support was taken up in 160 ml of 0.25M KPP buffer pH 8 containing 2% of glutardialdehyde, and the mixture was incubated for 2 hours under a water pump vacuum with gentle stirring. The mixture was subsequently refiltered and washed thoroughly with water.

Coupling of the enzyme:

The activated support was taken up in 200 ml of 1M KPP buffer with 10 µM pyridoxal phosphate (coupling buffer) and 130 mg/10.000 U enzyme and incubated overnight at 4° C.; the coupling yield was approximately 80%. This material was employed for transaminations as described in Example 16.

EXAMPLE 16

Continuous Synthesis of L-3-(2-thienyl)alanine Using Immobilized Enzyme 10 g of 2-hydroxy-3-(2-thienyl)acrylic acid, 9.3 g of L-aspartic acid, 20 mg of pyridoxal phosphate and 1 ml of mercaptoethanol were dissolved in 1000 ml of distilled water, and the mixture was brought to pH 8 using NaOH. The solution is cooled to 4° C. and used for the reaction. The catalyst used was accumulated enzyme (aromatic amino acid amino transferase from *E. coli* Z 1196/9), immobilized on a silica gel support (Grace XWP 500 MP, 0.5–1 mm), having a specific activity of 500–800 U per gram of dry support. 10 ml of the immobilizate were introduced into a column (40×18 mm internal diameter) which was heated at 40° C. using a heating jacket. The reaction solution was pumped through the column at a flow rate of 1.5 ml h$^{-1}$ and recooled to 4° C. The space-time yield obtained was 800 mg l$^{-1}$ h$^{-1}$ at a conversion rate of 50–60%. These values were achieved continuously over a period of 800 hours. L-3-(2-Thienyl) alanine was isolated analogously to Example 8.

We claim:

1. A compound of the formula III

in which $R^2$ is 4-bromo, 5-bromo, 3-methyl, 5-methyl or 5-nitro and $R^3$ has one of the following meanings a) 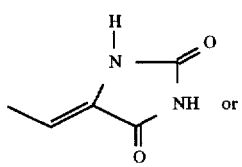 or
b) 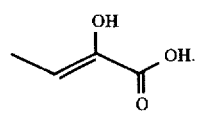
2. A compound of the formula IV
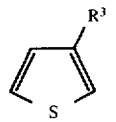 (IV)
in which $R^3$ has the following meaning:
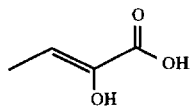
* * * * *